US00PP26367P3

(12) United States Plant Patent
Clark

(10) Patent No.: US PP26,367 P3
(45) Date of Patent: Feb. 2, 2016

(54) NECTARINE TREE NAMED 'AMOORE SWEET'

(50) Latin Name: *Prunus persica*
Varietal Denomination: Amoore Sweet

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 73 days.

(21) Appl. No.: 13/998,201

(22) Filed: Oct. 10, 2013

(65) Prior Publication Data

US 2015/0106982 P1 Apr. 16, 2015

(51) Int. Cl.
*A01H 5/08* (2006.01)
*A01H 5/00* (2006.01)

(52) U.S. Cl.
USPC ..... Plt./190
CPC ..... *A01H 5/00* (2013.01); *A01H 5/0856* (2013.01)

(58) Field of Classification Search
USPC ..... Plt./190
See application file for complete search history.

(56) References Cited

U.S. PATENT DOCUMENTS

PP12,620 P2 5/2002 Clark et al.
PP12,641 P2 5/2002 Clark et al.

OTHER PUBLICATIONS

Fresh Fruit Portal. Nov. 9, 2012.*
Clark, J.R. et al., "'Bowden' and 'Amoore Sweet' nectarines," (2013) HortScience 48(6):804-807.

* cited by examiner

*Primary Examiner* — Keith Robinson
(74) *Attorney, Agent, or Firm* — Andrus Intellectual Property Law, LLP

(57) ABSTRACT

Description and specification of a new and distinct nectarine tree cultivar named 'Amoore Sweet' which originated from a hand-pollinated cross of Ark. 699N×Ark. 663CN made in 2001. This new nectarine cultivar can be distinguished by its very firm, non-melting yellow flesh, early-mid season ripening, medium-sized fruits, excellent fruit quality with distinct low-acid nectarine flavor, and resistance to bacterial spot disease.

2 Drawing Sheets

Latin name: *Prunus persica.*
Varietal denomination: 'Amoore Sweet'.

BACKGROUND

A new cultivar of nectarine tree called 'Amoore Sweet' is described herein. The new cultivar originated from a hand-pollinated cross of Ark. 699N (non-patented, unreleased genotype) (female parent)×Ark. 663CN (non-patented, unreleased genotype) (male parent) made in 2001. The seeds resulting from this controlled hybridization were germinated in a greenhouse in the late winter 2001/early spring of 2002 and planted in a field near Clarksville, Ark. The seedlings fruited during the summer of 2004 and one seedling, designated Ark. 765, was selected for its very firm, non-melting yellow flesh, early-mid season ripening, medium-sized fruits, excellent fruit quality with distinct low-acid nectarine flavor, and resistance to bacterial spot disease.

SUMMARY OF THE INVENTION

The new and distinct cultivar of nectarine originated from a hand-pollinated cross of Ark. 699N (non-patented; female)×Ark. 663N (non-patented; male) made in 2001 near Clarksville, Ark. (West-Central Arkansas).

The seeds resulting from this controlled hybridization were germinated in a greenhouse in the late winter 2001/early spring of 2002 and planted in a field near Clarksville, Ark. The seedlings fruited during the summer of 2004 and one seedling, designated Ark. 765, was selected for its very firm, non-melting yellow flesh, early-mid season ripening, medium-sized fruits, excellent fruit quality with distinct low-acid nectarine flavor, and resistance to bacterial spot disease.

During 2004, the original plant selection was propagated asexually, at the above-noted location, by budding onto standard peach rootstock cultivar 'Lovell' (non-patented) and a test plot of two plants was established. Subsequently, larger test plantings have been established with asexually multiplied plants at two additional locations in Arkansas (near Clarksville and Hope, Ark.) and at each location propagation was by budding from buds collected at the Clarksville, Ark. test plot. No incompatibility with 'Lovell' peach rootstock has occurred following budding. During all asexual multiplication, the characteristics of the original plant have been maintained and no aberrant phenotypes have appeared.

The new cultivar has been named the 'Amoore Sweet' cultivar.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR 'AMOORE SWEET'

Figure 1:
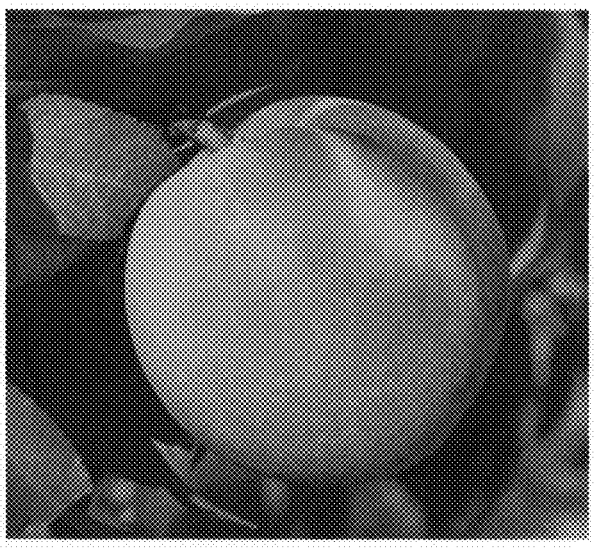
FIG. 1 is a photograph of mature fruit on a tree of 'Amoore Sweet' at six years of age.
Figure 2:
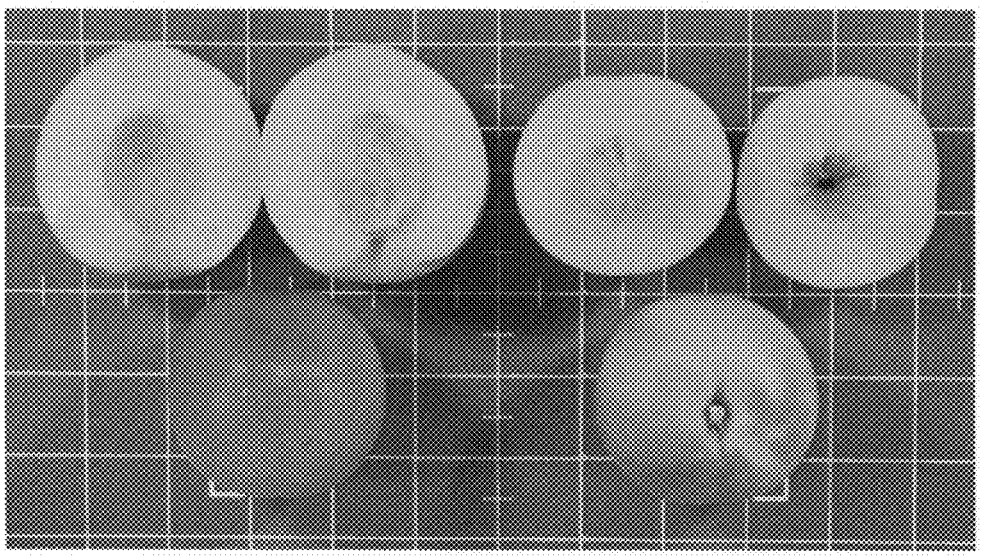
FIG. 2 is a photograph of a whole and longitudinally cut fruit of 'Amoore Sweet' at maturity at six years of age.
Figure 3:
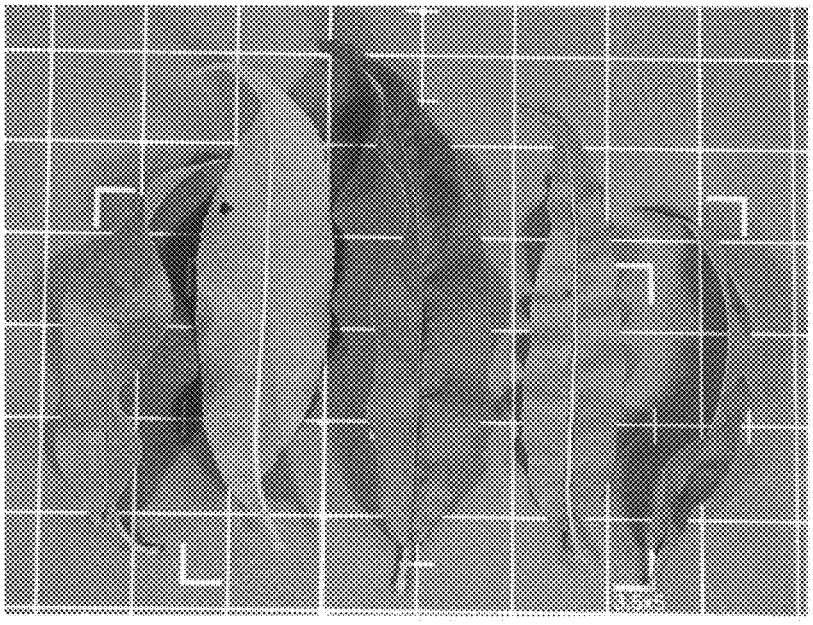
FIG. 3 is a photograph of the adaxial and abaxial sides of mature 'Amoore Sweet' leaves at six years of age.

Trees and fruit of this new cultivar differ phenotypically from its parents. The new cultivar is earlier ripening, firmer, higher in flavor, has low acidity, and has yellow, non-melting flesh compared to the female patent plant used in this hybridization, Ark. 669N, which is a low-acid, white nectarine selection with melting flesh or the 'Bowden' cultivar disclosed in U.S. patent application Ser. No. 13/998,198, which is a white nectarine selection with non-melting flesh and standard acid levels. The new cultivar is later ripening, with distinctly different low-acid flavor and flesh color compared to the male parent Ark. 663CN which has yellow flesh and flavor similar to a yellow nectarine. Both the parents and the instant variety are the genus and species *Prunus persica.*

Trees of the new cultivar are vigorous and productive, and trees are standard in size, well-branched and symmetrical with an upright to semi-spreading growth habit, comparable to other peach and nectarine trees. Trees express a high level of resistance to both foliar and fruit infection of bacterial spot [*Xanthomonas campestris* pv. *pruni* (Smith) Dye] but in some years do not show complete immunity to this disease. The new cultivar blooms in the spring on average 1 day earlier than 'Arrington' (U.S. Plant Pat. No. 12,641) and 2 days before 'Bradley'. (U.S. Plant Pat. No. 12,620). No winter cold injury has been observed on wood or buds of the new cultivar in Arkansas tests where minimum temperatures have reached 5° F. (15° C.) during evaluation. Chilling requirement to break dormancy is estimated to be 800 hours below 45° F. (7° C.).

Fruit of the new cultivar ripens early-midseason, averaging 5 days after 'Bradley' and 6 days after 'Arrington' reference nectarine cultivars. Average first ripening date is July 6 in west-central Arkansas (Clarksville). Fruit of the new cultivar has not been observed to have split pits, a serious fruit disorder of some peach and nectarine cultivars. Fruit yields have been good and comparable to those of the nectarine cultivars 'Arrington' and 'Bradley'.

The fruit is round in shape, and symmetrical. Fruits are attractive with an average 78% bright red blush. Fruit finish is good but, better than many nectarines grown at this test site due to reduced blemishes. The fruit skin has no pubescence, a major difference between peaches and nectarines. The flesh of the fruit is yellow in color and has no red pigment in the flesh. Flesh is of the non-melting type and is very firm at maturity. The fruit is a clingstone, in that the flesh adheres to the pit. Fruit size is medium-large averaging 145 g, slightly less than 'Bradley' (154 g) but larger than 'Arrington' (113 g).

The fresh fruit rates excellent in flavor and was rated highly in evaluations. Fruits average 17.3% soluble solids, higher than 'Bradley' with 14.8%. The flavor is sweet and low-acid with a distinct "mango-like" flavor. The acidity level of 'Amoore Sweet' of 0.29% malic acid compared to the standard acid 'Bradley' with 0.95% supports this flavor profile.

The following is a detailed description of the botanical and pomological characteristics of the subject nectarine. Color data are presented in Royal Horticultural Society Colour Chart designations (1986 2$^{nd}$ edition). Where dimensions, sizes, colon and other characteristics are given, it is to be understood that such characteristics are approximations of averages set forth as accurately as practical.

Plants used for botanical data were six years old and grown on a fine sandy loam soil with trickle irrigation near Clarksville, Ark. Trees were trained to an open-center training system and dormant pruned annually. The exception to this is that yield data was collected on trees four years old and trained to perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were made to the trees, but no bactericides (for control of bacterial diseases such as bacterial spot disease) were applied. The descriptions reported herein are from specimens grown near Clarksville, Ark.

Plant:

*Size.*—Mature trees (6 years of age) average 3.5 m to 3.8 m in height and 4.8 to 6.0 m in spread or width, and a semi-upright growth habit, as grown on 'Lovell' rootstock using an open-center training system commonly used on peaches and nectarines. Tree size is comparable to that of the 'Bradley' and 'Arrington' cultivars.

*Growth.*—Vigorous, symmetrical form, good canopy development. Vigor comparable to that of 'Bradley' and 'Arrington' cultivars.

*Productivity.*—Very productive and consistent from year to year. Yield measured 14.4 kg /tree in 2010 in a 2007-planted replicated trial compared to 13.2 kg/tree for 'Bradley' and 11.2 kg/tree for 'Arrington'. Crop load ratings on a 10-point scale (with 10=high yield potential) for 'Amoore Sweet' averaged 8.7 while 'Arrington' 8.5, and 'Bradley' 8.0 in six years of observation.

*Cold hardiness.*—Wood and dormant buds hardy to 5° F. (15° C.), as this was the coldest the trees were exposed to at the test site but hardiness may exceed this temperature.

*Disease resistance.*—Leaves and fruit resistant but not immune to bacterial spot (*Xanthomonas campestris* pv. *Pruni* (Smith) Dye) under growing conditions where bacterial spot infection is often very severe on susceptible genotypes. No bactericides were used in the development or evaluation of the instant cultivar. Evidence of bacterial spot infection was less than that of 'Arrington' and comparable to 'Bradley' in all years of evaluation. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thüm.) Oudem) the other common diseases at Clarksville, Ark., was determined.

*Insect resistance.*—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stål); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (*Synathedon pictipes* (Grote & Robinson)), and greater peach tree borer (*Synanthedon exitiosa* (Say)). Therefore no insect resistance was determined in the testing of the instant cultivar.

Foliage/shoots/branches:

*Shoots.*—Smooth. Dormant-season shoot (branch): length 67.2 cm; diameter at base 0.6 cm; diameter at midpoint 0.4 cm; diameter at terminal 0.3 cm. Dormant-season shoot color Greyed-Orange Group (172A) on one side and Yellow-Green Group (146C) on the side with greater light exposure.

*Leaves.*—Simple, alternate, glabrous, lanceolate, petiolate, deciduous. Venation pinnate; base acute; terminal or apex acuminate; margin serrated. Mature leaf size: length 15.7 cm; width midpoint 14.9 cm. Leaf serrations 4.3/cm. Mature leaf color: abaxial — Green Group (139A); adaxial — Green Group (137A); and anthocyanin not present on abaxial or adaxial side of mature leaves on midrib or other location. Young leaf color: abaxial — Green Group (139C); adaxial — Green Group (137A); anthocyanin not present on abaxial or adaxial side of young leaves on midrib or other location. Petiole length — mature leaf: 1.5 cm; petiole width: 1.394 mm; petiole texture: smooth no pubescence; petiole strength: strong. Leaf glands: reniform, average of 3.2 per leaf, located at base of leaf blade at top of petiole; Stipule length: 8.316 mm.

*Buds.*—Number of leaf buds per 15 cm: 7. Number of flower buds per 0-15 cm from terminal: 10. Mature shoot internode length: base 1.9 cm, midpoint 2.3 cm, terminal 1.9 cm.

Bark (of mature trunk of tree):

*Color.*—Greyed-Green Group (198A).

*Texture.*—Rough.

Trunk:

*Diameter.*—12.7 cm (at 25 cm above ground level).

Flower buds: Dormant flower bud length 0.5 cm and diameter 0.3 cm and color Greyed-Green Group (197C); dormant buds swell and expand in late winter and increase in size during this expansion to fully open flowers.

Flowers: Bloom occurs prior to vegetative bud break; solitary to occasional double individual flowers at a single node; perfect; self-fertile.

*Date of bloom.*—First, Julian 79 (March 19); Full, Julian 82 (March 22); full bloom for 'Bradley' and 'Arrington' March 24.

*Size.*—Diameter fully open 2.0 cm.

*Type.*—Non-showy.

*Color.*—Adaxial: Red Group (54A); abaxial: Red Group (54A).

*Petals per flower.*—5.

*Petal dimensions.*—Length 12.2 mm; width 7.0 mm; texture smooth.

*Length of pistil.*—1.5 cm.

*Stamens.*—Average 49/flower with pollen present, fertile and abundant.

*Ovary.*—Smooth.

*Pollen.*—Color: yellow green group 152-A.

Fruit:

*Size.*—Medium-large, avg. 145 g; slightly less than 'Bradley' (154 g) but larger than 'Arrington' (113 g); diameter stem end 3.5 cm, equator 6.4 cm, blossom end 2.3 cm; length base to apex. 6.7 cm.

*Shape.*—Round, symmetrical with no tip.

*Skin.*—Smooth, attractive; ground color Yellow-Orange Group (23A), with red blush (Red Group 53A), about 78% of surface on average.

*Flesh.*—Yellow-Orange Group (21A); clingstone; uniform non-melting texture, non-rubbery. Firmness when measured by a fruit pressure tester (using a McCormick model FT327 fruit pressure tester, 11 mm diameter probe, McCormick Fruit Tree Co., Yakima, Wash.) on unpeeled fruit had average firmness value of 5.8 kg. Excellent eating quality; flavor sweet, low-acid.

*Pedicel length.*—0.5 cm.

*Pedicel diameter.*—0.5 cm.

*Pedicel color.*—Yellow-Green Group (149A).

*Pedicel strength.*—Holds on well; takes some effort to twist off.

*Glossiness.*—Strong.

*Ripe date.*—July 6 (Julian 186) in west-central Arkansas; 5 days after 'Bradley' and 6 days after 'Arrington'. Ripening of individual fruit is uniform.

*Tendency of pit to split.*—No split pits most years.

*Soluble solids.*—17.3% soluble solids.

*Fruit juice pH.*—4.1.

*Tritratable acidity.*—0.29% malic acid compared to 'Bradley' with 0.95%.

*Storage performance.*—Overall ranking of 4.7 for 0-3 weeks of storage and higher than 'Bradley' (3.7) on a 5-point scale with 5 being exceptional storage. Further ratings for storage characteristics for 'Amoore Sweet' indicate exceptional performance for all variables, specifically browning, mealiness, and flesh color and quality throughout storage.

Pit/stone:

*Size.*—Length 3.8 cm; diameter (midpoint) 2.0 cm.

*Shape.*—Slightly oblong with deep furrowing and pitting.

*Color.*—Greyed-Orange Group (167A).

Kernel:

*Size.*—Length 1.7 cm; diameter varies with dryness of the kernel but is up to 0.5 cm.

*Shape.*—Almond.

*Color.*—Greyed-Orange Group (167A).

Uses: Fresh consumption, not evaluated for drying or other uses.

The Cultivar

The most distinctive features of the new cultivar are its very firm, non-melting yellow flesh, early-mid season ripening, medium-sized fruits, excellent fruit quality with distinct low-acid nectarine flavor, and resistance to bacterial spot disease.

I claim:

1. A new and distinct cultivar of nectarine tree named 'Amoore Sweet,' substantially as illustrated and described.

* * * * *